United States Patent
Stensrud

(10) Patent No.: US 10,081,611 B2
(45) Date of Patent: Sep. 25, 2018

(54) METHOD FOR ACID-CATALYZED ACYLATION OF THE REDUCTION PRODUCTS OF 5-HYDROXYMETHYL FURFURAL

(71) Applicant: Archer Daniels Midland Company, Decatur, IL (US)

(72) Inventor: Kenneth Stensrud, Decatur, IL (US)

( * ) Notice: Subject to any disclaimer, the term of this patent is extended or adjusted under 35 U.S.C. 154(b) by 0 days.

(21) Appl. No.: 15/527,981

(22) PCT Filed: Nov. 21, 2014

(86) PCT No.: PCT/US2014/066836
§ 371 (c)(1),
(2) Date: May 18, 2017

(87) PCT Pub. No.: WO2016/081010
PCT Pub. Date: May 26, 2016

(65) Prior Publication Data
US 2017/0327480 A1 Nov. 16, 2017

(51) Int. Cl.
| | |
|---|---|
| *C07D 307/12* | (2006.01) |
| *C07D 307/42* | (2006.01) |
| *B01J 31/00* | (2006.01) |
| *B01J 31/02* | (2006.01) |

(52) U.S. Cl.
CPC ............ *C07D 307/12* (2013.01); *B01J 31/00* (2013.01); *B01J 31/0225* (2013.01); *C07D 307/42* (2013.01)

(58) Field of Classification Search
CPC ...... C07D 307/12; C07D 307/42; B01J 31/00; B01J 31/0025
See application file for complete search history.

(56) References Cited

U.S. PATENT DOCUMENTS 8,242,293 B2 * 8/2012 Gruter ................. C07D 307/46
44/350

* cited by examiner

*Primary Examiner* — Timothy R Rozof
(74) *Attorney, Agent, or Firm* — William B. Miller

(57) ABSTRACT

An improved process for acid-catalyzed acylation using water-tolerant Lewis acid catalysts is described. The method involves reacting a reduction products of 5-(hydroxylmethyl)-furfural (HMF), in particular either furan-2,5-dimethanol (FDM) or bis-2,5-(hydroxymethyl)-tetrahydrofuran (bHMTHFs), with an excess of an organic acid in the presence of a Lewis acid metal triflate at a temperature and time sufficient to produce esters. The conversions of the reduction products of HMF to corresponding diesters can be quantitative with certain favored Lewis acids catalysts.

20 Claims, 6 Drawing Sheets

METHOD FOR ACID-CATALYZED ACYLATION OF THE REDUCTION PRODUCTS OF 5-HYDROXYMETHYL FURFURAL

CLAIM OF PRIORITY

The present application is a national stage entry of International Application No. PCT/US2014/066836, filed 21 Nov. 2014, the contents of which are herein incorporated by this reference.

FIELD OF INVENTION

The present disclosure relates to sugar-derived diols that can be used as monomers for polymer synthesis, as well as precursors to various industrial chemicals. In particular, the present invention pertains to furanic esters and methods for their synthesis.

BACKGROUND

Conventionally, commodity chemicals have been made largely from fossil or petroleum-based hydrocarbons. In recent years as interest in renewable resources has grown, advances in more efficient technologies have enabled renewable or "green" feedstocks to become viable economic substitutes. One class of renewable biologically-derived hydrocarbon resources has been derived from sugars. However, because of the inherent complex functionalities of sugar molecules which can readily degrade, particularly at higher temperatures, these materials have traditionally received limited attention for industrial uses.

Recent research efforts have concentrated on the production of sugar-based feedstocks with less functionality. Furans are a variety of versatile molecular platforms that can be derived readily from sugars. These molecules have structural features particularly useful in preparing polymers, pharmaceuticals, or solvents, among other industrial constituents.

A compound that has attracted attention is 5-(hydroxylmethyl)-furfural (HMF), the principal dehydration product of fructose, a cheap and plentiful monosaccharide (Scheme A).

Scheme A. Acid catalyzed dehydrative cyclization of fructose, producing HMF

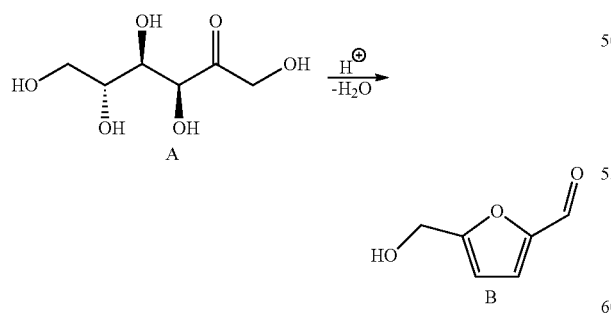

The dual alcohol and aldehyde moieties of HMF enable it to be used as precursor for many potential industrial materials such as polymers, solvents, surfactants, and pharmaceuticals.

A drawback to employing HMF directly has been its predisposition to readily polymerize and oxidatively degrade in the presence of air, hence necessitating the presence of an antioxidant to improve longevity. HMF can be reduced to more stable molecules, such as furan-2,5-dimethanol (abbreviated as FDM) and bis-2,5-(hydroxymethyl)-tetrahydrofuran (abbreviated as bHMTHF), illustrated in Scheme B.

Scheme B.
Structures of a) FDM and b) cis, c) trans diastereomers of bHMTHF

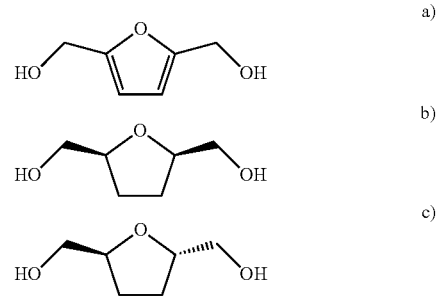

FDM is produced from partial hydrogenation (aldehyde reduction) of HMF as depicted in Scheme C, while exhaustive hydrogenation engenders the saturated analog bHMTHF, typically produced in a 9:1 cis to trans diastereometic proportion as in Scheme D. (See e.g., U.S. Pat. Nos. 7,317,116, or 7,393,963 B2.)

Scheme C. FDM from partial hydrogenation of HMF

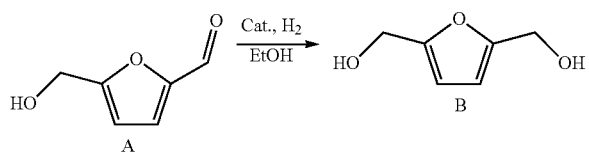

Scheme D. cis/trans bHMTHF from the exhaustive catalytic reduction of HMF

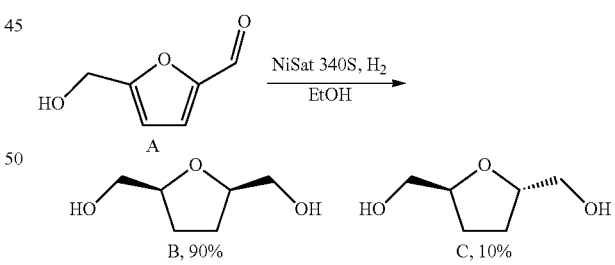

The bifunctional nature of these compounds enables them to be readily deployed as starting materials in a various chemical syntheses, and as practicable replacements for petroleum-based aromatic hydrocarbons. These materials can be valuable precursors, for example, to polyesters, polyurethane foams, plasticizers, resins, surfactants, dispersants, lubricants, agricultural chemicals, or as a solvents, binders, or humectants. The hydroxymethyl appendages at the 2 and 5 loci of the tetrahydrofuran ring provide two chiral centers, which permit bHMTHFs to be possible scaffolds for pharmaceuticals or chiral auxiliaries in the emerging realm of asymmetric organic synthesis. The applications of FDM and bHMTHFs demands both cost effective and streamlined methodologies that afford large scale manufacture of these compounds from HMF.

Exploration into preparation of molecular derivatives using FDM and/or bHMTHFs has been constrained by the prohibitive cost (e.g., ~$200 per gram commercially) of these raw materials. To effectively compete with chemical precursors derived from fossil-based hydrocarbon sources, the preparation of HMF derivatives from common agricultural sources requires better ways of converting and producing desired derivative and intermediate compounds. Until recently, large-scale commercialization of furanics has been comparatively cost inefficient.

One approach to enhance the use FDM and bHMTHF as starting platforms for precursors or feedstocks is to convert them to esters. The established commercial synthesis of esters typically entails direct alcohol acylation with carboxylic acids catalyzed by a Brønsted acid. This protocol is commonly specified as the Fischer-Speier esterification. Typically, strong inorganic acids such as $H_2SO_4$ and HCl are employed as the catalyst. These strong acids are readily obtained, inexpensive materials but are difficult to regenerate, which increases the waste stream. Additionally, these acids can react in an undesired manner by the addition of their anionic moiety forming byproducts such as sulfate esters.

Although some robust processes have evolved recently where higher purities are attained. (See generally, X. Tong et al., "Biomass into Chemicals: Conversion of Sugars to Furan Derivatives by Catalytic Processes," APPLIED CATALYSIS A: GENERAL 385 (2010) 1-13.), the problem of developing more efficient purification still persists.

Efforts to overcome these issues using solid resin catalysts have been tried but have been unsuccessful for large volumes. Unfortunately, traditionally employed solid acids are not hydrolytically stable and even trace amounts of water can negatively impact the catalytic activity. Homogeneous metal catalysts have also shown limited activity owing to their susceptibility to hydrolyze, which reduces the catalytic activity.

In view of these drawbacks with convention processes a need still exists for a process in which one can attain higher ester yields at economical catalyst loadings for the preparation of HMF-derived compounds for use as precursors.

SUMMARY OF INVENTION

The present disclosure relates, in part, to a method for acid-catalyzed acylation of a reduction product of 5-(hydroxylmethyl)-furfural (HMF), in particular either furan-2,5-dimethanol (FDM) or bis-2,5-(hydroxymethyl)-tetrahydrofuran (bHMTHF). The method involves reacting the FDM or bHMTHF and an excess of an organic acid in a reaction in the presence of a water-tolerant Lewis acid catalyst at a reaction temperature and for a time sufficient to produce a corresponding ester product mixture. The esterification is performed at a temperature in a range from about 150° C. to about 250° C.

Additional features and advantages of the present process will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I.—Description

Figure 1:
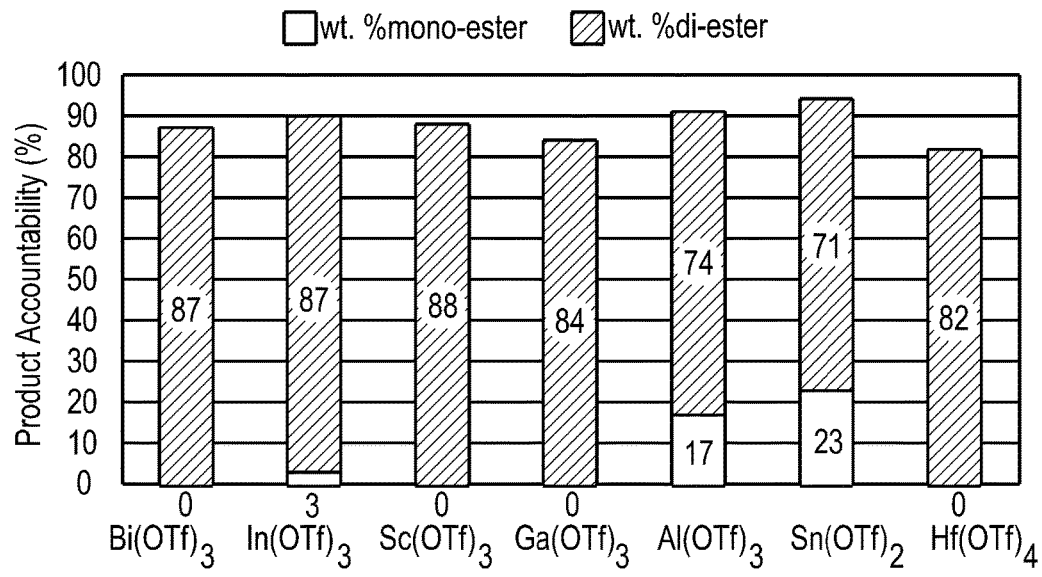
FIG. 1, shows the composition of several product mixtures prepared according to examples of acid-catalyzed acylation of bHMTHF using various water-tolerant Lewis acid catalysts (metal triflates), each at a catalyst load of 0.1 wt. % relative to the amount of bHMTHF.

Furan-2,5-dimethanol (FDM) and ((2R,5S)-tetrahydrofuran-2,5-diyl)dimethanol and ((2S,5S)-tetrahydrofuran-2,5-diyl)dimethanol (bHMTHFs), which are obtained from the reduction of HMF, are promising renewable molecular surrogates for conventional petroleum-derived chemical feedstocks. To facilitate transformation of these reduced molecules into feedstocks for various uses, the reduction products can be converted into mono and diesters by means of acylation. The resulting mono- and diesters of HMF reduction products can be employed for instance as precursors to polymers, plasticizers, lubricants, and chemical additives.

The present disclosure describes a transformation that employs homogeneous water-tolerant Lewis acid catalysts, which can enable facile, direct acylation with an organic acid to generate mono- and diesters of FDM and bHMTHFs. The ability of water-tolerant metal catalysts to generate relatively high diester yields (e.g., ≥55%-60%) at reduced catalyst loads is highly desirable and can improve process economics relative to conventional strong Brønsted acids (e.g., sulfuric or p-toluenesulfonic acids). Conventional, large-scale Fischer-Speier esterification (FSE) typically use at least 1 mol. % of acid catalyst loads per mole of alcohol reactant. In contrast, the present method of esterification can use two or three orders of magnitude less catalyst to attain commensurate ester yields. The Lewis acid catalyst can be present, for instance, in as small an amount as about 0.01 mol. % relative to the amount of HMF reduction products. Hence, the present method can help significantly towards cost controls while concurrently augmenting the overall process efficiency.

Water-tolerant Lewis acids have received attention in facilitating many chemical transformations, and are reviewed thoroughly in *Chem Rev,* 2002, 3641-3666, the contents of which are incorporated herein by reference. Traditionally, Lewis acids favor conditions in which virtually no water moisture is present, as they can quickly hydrolyze and lose their catalytic function even with minor or trace amounts of water. As used herein, the term "water-tolerant" refers to a characteristic of a metal ion of a particular catalyst to resist being hydrolyzed by water to a high degree. Metal trifluoromethanesulfonate ($CF_3SO_3^-$), also commonly referred to as triflates (-OTf), possess this remarkable trait, (e.g., see, *J. Am. Chem. Soc.* 1998, 120, 8287-8288, the content of which is incorporated herein by reference). For the methods disclosed herein, water-tolerant Lewis acids that demonstrate good reactivity may include one or more metal triflates, for example, of hafnium (IV), gallium (III), bismuth (III), scandium (III), indium (III), yttrium, copper (II), mercury, nickel, zinc, aluminum, iron, thallium, or tin (II)). In other embodiments the metal triflate species can be of a Lanthanide rare-earth metal (i.e., cerium, praseodymium, neodymium, samarium, europium, gadolinium, terbium, dysprosium, holmium, erbium, ytterbium, lutetium). In certain favored embodiments, the water-tolerant catalyst is a triflate of gallium, scandium, bismuth, hafnium, indium, aluminum or tin.

In general, the present method for acid-catalyzed acylation entails contacting the reduction product of HMF with an organic acid in the presence of a metal triflate catalyst at a temperature up to about 250° C. for a period of up to about 12 hours. The reaction temperature can be from about 150° C. or 160° C. to about 240° C. or about 250° C., inclusive of any range therein between. Typically, the reaction temperature is in a range from about 170° C. or 180° C. to about 200° C. or 220° C. The reaction time can be between about 30 or 45 minutes and 6 hours. Typically, the reaction time is within about 1-4 hours, more typically about 2 or 3 hours.

The organic acid reagent can be an alkanoic acid, alkenoic acid, alkyonoic acid, or aromatic acid, having a carbon chain length ranging from $C_2$-$C_{26}$. In particular examples, the organic acid is 2-ethylhexanoic acid, hexanoic acid, and octanoic acid. The concentration of organic acid used is in molar excess about 2-fold to about 10-fold of the amount of HMF reduction product. Usually, the amount of organic acid is in molar excess about 3-fold to about 5-fold.

The catalyst load for water-tolerant Lewis acids can be less than about 1 mol. % relative to the concentration of HMF reduction products. In certain embodiments, the metal triflate catalyst can be present in an amount as low as about 0.001 mol. %. Typically, the amount of catalyst loading is about 0.5 mol. % or less. Depending on the desired product mixture, catalyst levels are usually in a range from about 0.1 mol. % to about 0.01 mol. %, more typically about 0.03 mol. % or 0.05 mol. %. When the amount catalyst is at about 0.1 mol. % or more, one achieves full acylation of the HMF reduction products and diesters are the primary products in ≥60% yields. In other embodiments, when the catalyst is present in an amount between about 0.01 mol. % and 0.1 mol. %, the chief acylation products are a mixture of corresponding mono and diesters. In further embodiments, when the amount of catalyst present is an amount <0.01 mol. %, the product mixture contains predominantly monoesters and unreacted HMF reduction products.

Conversion yields of the HMF reduction products to corresponding mono or diesters are ≥55% or 60%. Typically, the conversion is high (e.g., ≥80%, 85%, or 90%). Diesters can be the primary product (e.g., ≥60%) of the product mixture with sufficient concentration of catalyst. The ester product mixture contains ≥10% yield of diesters. Typically, the yield of diester is from about 15% to about 85% in the ester product mixture (e.g., 60% to 75% or 80%). In certain favored embodiments, most to all (e.g., about 80% to 100%) of the HMF reduction product is converted to its corresponding diester species.

Another advantage of the present methods for preparing esters is the ability to maintain high product accountability of at least 80%, as shown in the accompanying Tables. Typically, the percentage accountability is ≥85%. "Accountability" as used herein, is a measure of the percentage of the product mixture that can be quantitatively identified as targeted ester compounds and unreacted starting material, while excluding poly-condensates, color bodies or other species that are not identified as ester products. Thus, the total accountability for each product mixture is the combined amount of the mono- and diester products and any unreacted starting material.

A. Preparation of bHMTHF Esters

According to an example of the a method described herein, Scheme 1 depicts an esterification reaction of bHMTHFs with 2-ethylhexanoic acid catalyzed using a metal triflate as represented generically as $M(Otf)_x$. The reaction is performed neat at a temperature of 175° C. for 3 h. The particular species of metal triflate used is determined with respect to the desired level of catalyst reaction kinetics and desired ratio of mono and diester products. (Lewis acid activity of the examples in descending order is: Hf>Ga>Sc>Bi>In>Al>Sn.) The reaction generates a product mixture that may contain both mono or diesters. Given the chiral nature of the bHMTHF molecule, a mix of cis and trans products is present in a 9:1 ratio.

Scheme 1: Acid-catalyzed acylation of bHMTHF.

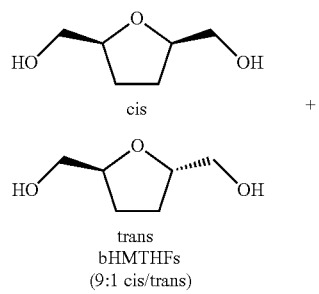

bHMTHFs
(9:1 cis/trans)

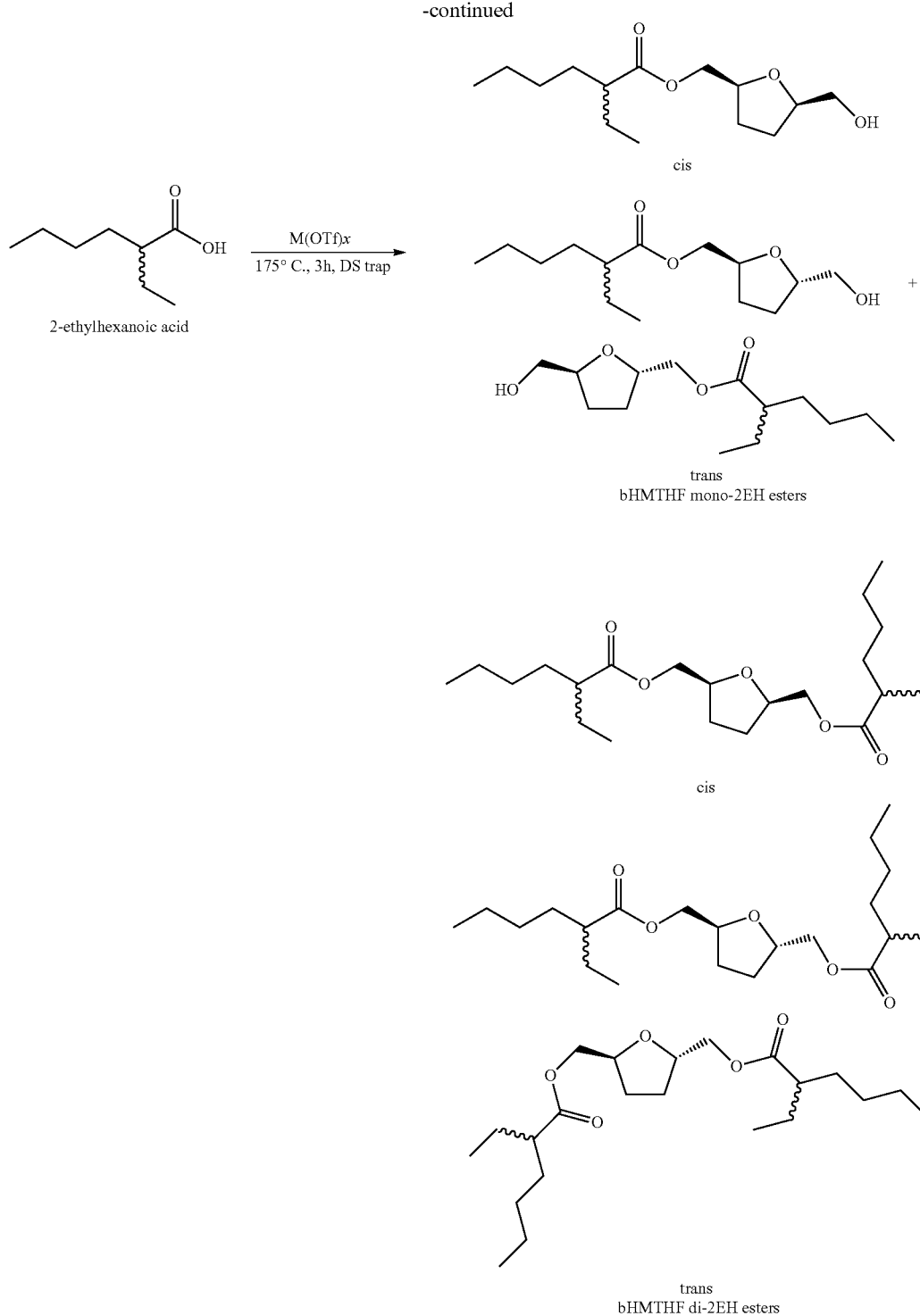

M = Hf, Ga, Sc, Bi, In, Al, Sn
x = 2,3,4

Table 1 summarizes data for several water-tolerant Lewis acid-catalyzed acylations of bHMTHF with 2-ethylhexanoic acid each at 0.1 mol. % catalyst loads. The data includes the amount of mono and diester yield and overall product mixture accountability of each reaction. Also shown is the product mixture of an esterification conducted using a conventional strong Brønsted acid catalyst, sulfuric acid ($H_2SO_4$), also at a catalyst load of 0.1 mol. % of the bHMTHF. All of the water-tolerant Lewis acid catalysts perform significantly better in the synthesis of the diester compared to the reaction catalyzed using sulfuric acid.

TABLE 1

| Ex. | Catalyst | Catalyst Loading (mol. %) | Time (h) | Temp. (° C.) | Conversion (wt. % bHMTHF) | Mono-2EH wt. % | Di-2EH wt. % | Product Accountability wt. % |
|---|---|---|---|---|---|---|---|---|
| 1 | Bi(OTf)$_3$ | 0.1 | 3 | 175 | 100 | 0 | 87 | 87 |
| 2 | In(OTf)$_3$ | 0.1 | 3 | 175 | 100 | 3 | 87 | 90 |
| 3 | Sc(OTf)$_3$ | 0.1 | 3 | 175 | 100 | 0 | 88 | 88 |
| 4 | Ga(OTf)$_3$ | 0.1 | 3 | 175 | 100 | 0 | 84 | 84 |
| 5 | Al(OTf)$_3$ | 0.1 | 3 | 175 | 100 | 17 | 74 | 91 |
| 6 | Sn(OTf)$_2$ | 0.1 | 3 | 175 | 100 | 23 | 71 | 94 |
| 7 | Hf(OTf)$_4$ | 0.1 | 3 | 175 | 100 | 0 | 82 | 82 |
| Comp. 1 | H$_2$SO$_4$ | 0.1 | 3 | 175 | 100 | 8 | 66 | 74 |

FIG. 1 presents in graphical form the data in Table 1. The graph arranges different metal triflate catalysts along the x-axis and measures the percent product accountability from 0-100% for each of the reactions on the y-axis. The product mixtures of reactions catalyzed with each of the metal triflate species exhibits at least 80% accountability. This is greater than the value for product compositions of a reaction catalyzed with sulfuric acid (i.e., 74%).

Figure 2:
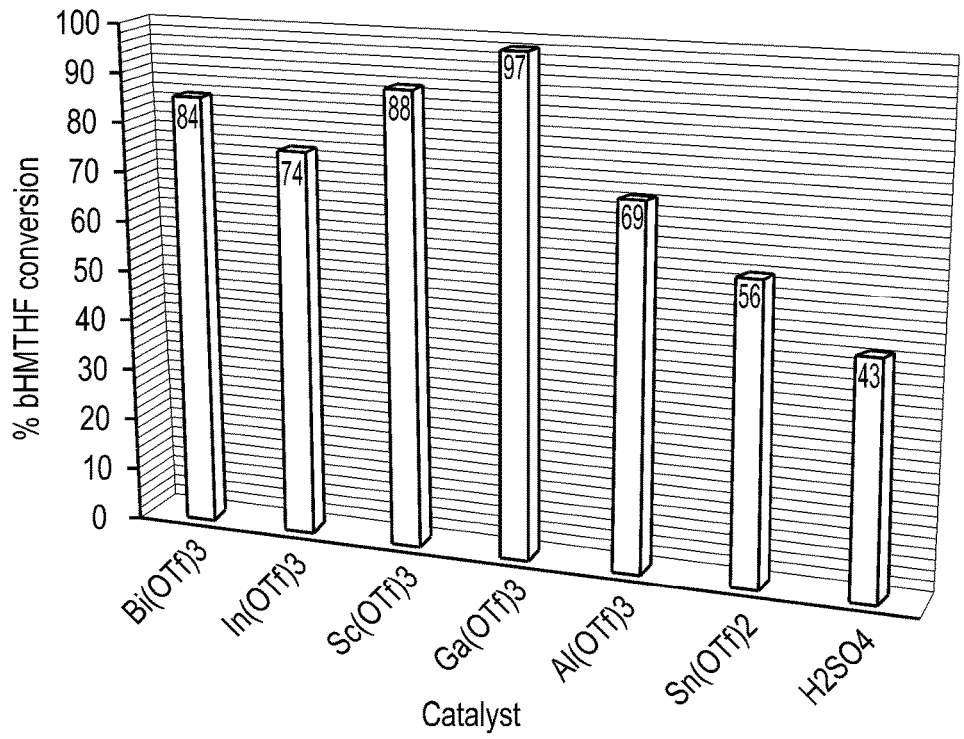
FIG. 2, shows a comparison of the amount of bHMTHF converted to esters in reactions catalyzed with certain Lewis acid catalysts presented in Figure 1 and sulfuric acid.
Figure 3:
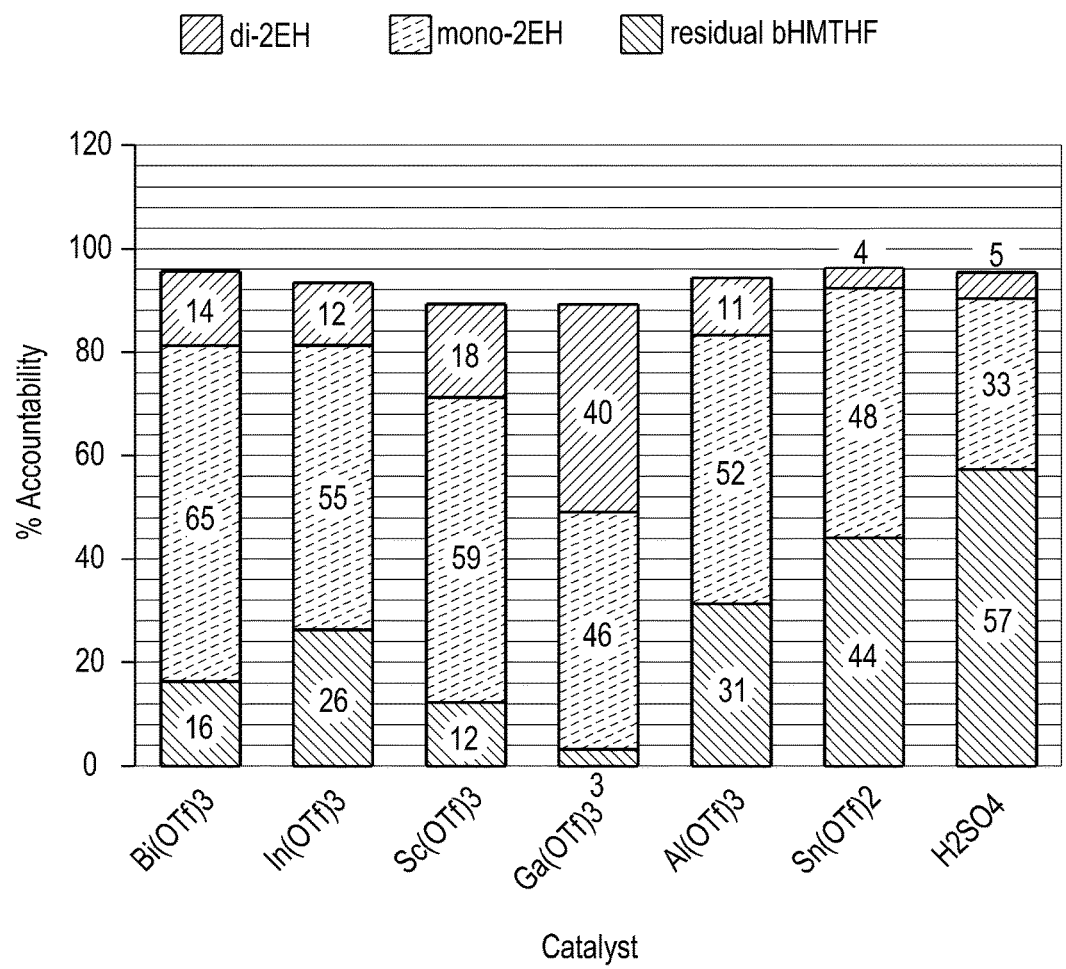
FIG. 3, shows the composition of several product mixtures prepared according to examples of acid-catalyzed acylation of bHMTHF using various water-tolerant Lewis acid catalysts (metal triflates), each at a catalyst load of 0.01 wt. % relative to the amount of bHMTHF.

Table 2 presents a summary of the comparative conversion rates in wt. % of bHMTHF to its corresponding ester products and overall product accountability when catalyzed using water-tolerant Lewis acids and a conventional Brønsted acid, sulfuric, each at 0.01 mol. % catalyst loads. Each of the metal triflate Lewis acid species converts more than 50% of the bHMTHF to an ester. In comparison, the sulfuric acid catalyst converts 43% of the bHMTHF to an ester. For particular Lewis acid species, such as Sc(OTf)$_3$, Ga(OTf)$_3$, and Hf(OTF)$_4$, the conversion rate is at least double of that for the sulfuric acid catalyst. Generally, the amount of mono- and diesters generated with the Lewis acid catalysts are also greater than that of the sulfuric acid catalyzed reaction. FIG. 2 is a graphical representation of the conversion rate. FIG. 3 presents the amount of unreacted bHMTHF (wt. %), mono- and diester yields, and overall product accountability for the reactions of Table 2.

Overall product accountability levels are comparable, within about 5-10%, for the reaction using Lewis acid catalysts and the sulfuric acid catalyst. For instance in Comparative Example 1 of Table 2, a reaction catalyzed using sulfuric acid (0.01 mol. %) has a product accountability of 95%. The reaction generates about 33 wt. % monoesters, 5 wt. % diesters, and the majority (57%) of bHMTHF remains unreacted. In contrast, in Example 1, the reaction catalyzed with Bi(OTf)$_3$ at 0.01 mol. % also exhibits 95% product accountability, composed of about 65 wt. % monoester, 14 wt. % diester, and 16 wt. % unreacted bHMTHF. The overall product accountability is the same for these two examples, but the amount of mono or diesters produced is significantly more for the Lewis acid catalyzed reaction.

Likewise in the other examples, the ester products from other metal triflate reactions at the same low catalyst load show improved conversion rates and yields over sulfuric acid. Generally, the Lewis acid catalyzed ester product mixture exhibits at least the same level, if not better product accountability as a product mixture from a reaction catalyzed with a strong Brønsted at the same catalyst load. In other words, the Lewis acid catalyzed reactions tend to form minimal side products for a cleaner product mix.

TABLE 2

Summary of water-tolerant Lewis acid (metal triflate) and Brønsted acid catalyzed acylation of bHMTHF with 2-ethylhexanoic acid at 0.01 mol % loadings.

| Ex. | Catalyst | Catalyst Loading (mol. %) | Time (h) | Temp (° C.) | Conversion (wt. % bHMTHF) | bHMTHF wt. % | Mono-2EH wt. % | Di-2EH wt. % | Product Accountability wt. % |
|---|---|---|---|---|---|---|---|---|---|
| 1 | Bi(OTf)$_3$ | 0.01 | 3 | 175 | 84 | 16 | 65 | 14 | 95 |
| 2 | In(OTf)$_3$ | 0.01 | 3 | 175 | 74 | 26 | 55 | 12 | 94 |
| 3 | Sc(OTf)$_3$ | 0.01 | 3 | 175 | 88 | 12 | 59 | 18 | 89 |
| 4 | Ga(OTf)$_3$ | 0.01 | 3 | 175 | 97 | 3 | 46 | 40 | 89 |
| 5 | Al(OTf)$_3$ | 0.01 | 3 | 175 | 69 | 31 | 52 | 11 | 93 |
| 6 | Sn(OTf)$_2$ | 0.01 | 3 | 175 | 56 | 44 | 48 | 4 | 96 |
| 7 | Hf(OTf)$_4$ | 0.01 | 3 | 175 | 100 | 0 | 52 | 36 | 88 |
| Comp 1 | H$_2$SO$_4$ | 0.01 | 3 | 175 | 43 | 57 | 33 | 5 | 95 |

Table 3 illustrates that a change in concentration of catalysts can have a significant impact on bHMTHF conversion rates and type and ratio of mono and diester product made. In Examples 1-14, several different metal triflate species are presented at 0.1 mol. % and 0.01 mol. % catalyst loadings relative to the amount of bHMTHF. Comparing the results of FIGS. 1 and 3 demonstrates the difference that an order of magnitude in catalyst loading can make. For the more active metal triflate species, all of the bHMTHF is reacted with the greater catalyst amount.

Comparative Example 1 of Table 3 shows the result of a reaction catalyzed with p-toluenesulfonic acid (p-TsOH), another strong Brønsted acid. The amount of metal triflate catalyst used in each of the Examples is one or two orders of magnitude less than the amount of p-TsOH catalyst used to perform the same reaction. The results from the two kinds of acid catalysts are comparable with regard to bHMTHF conversion rate as well as monoester and diester product yields. This feature demonstrates that the present methods of esterification using water-tolerant Lewis acid catalysts can contribute to process cost savings.

TABLE 3

2EH acylation of bHMTHF (9:1). 3 mol. equivalents of 2EH per bHMTHF

| Ex. | Catalyst | Loading (mol. %) | Time (h) | Temp (° C.) | Conversion (wt. % bHMTHF) | Mono-2EH wt. % | Di-2EH wt. % | Accountability wt. % |
|---|---|---|---|---|---|---|---|---|
| 1 | Bi(OTf)₃ | 0.1 | 3 | 175 | 100 | 0 | 100 | 87 |
| 2 | Bi(OTf)₃ | 0.01 | 3 | 175 | 84 | 65 | 14 | 95 |
| 3 | In(OTf)₃ | 0.1 | 3 | 175 | 100 | 3 | 87 | 90 |
| 4 | In(OTf)₃ | 0.01 | 3 | 175 | 74 | 55 | 12 | 94 |
| 5 | Sc(OTf)₃ | 0.1 | 3 | 175 | 100 | 0 | 100 | 88 |
| 6 | Sc(OTf)₃ | 0.01 | 3 | 175 | 88 | 59 | 18 | 89 |
| 7 | Ga(OTf)₃ | 0.1 | 3 | 175 | 100 | 0 | 100 | 84 |
| 8 | Ga(OTf)₃ | 0.01 | 3 | 175 | 97 | 46 | 40 | 89 |
| 9 | Al(OTf)₃ | 0.1 | 3 | 175 | 100 | 17 | 74 | 91 |
| 10 | Al(OTf)₃ | 0.01 | 3 | 175 | 69 | 52 | 11 | 93 |
| 11 | Sn(OTf)₂ | 0.1 | 3 | 175 | 100 | 23 | 71 | 94 |
| 12 | Sn(OTf)₂ | 0.01 | 3 | 175 | 56 | 48 | 4 | 96 |
| 13 | Hf(OTf)₄ | 0.1 | 3 | 175 | 100 | 0 | 100 | 82 |
| 14 | Hf(OTf)₄ | 0.01 | 3 | 175 | 100 | 52 | 36 | 88 |
| Comp. 1 | p-TsOH | 1 | 3 | 175 | 100 | 14 | 70 | 84 |

B. Preparation of FDM Esters

The esterification of FDM according to another embodiment of present method is similar to the reactions described for bHMTHF. According to the example shown in Scheme 2, FDM reacts with 2-ethylhexanoic acid in an acylation catalyzed by hafnium triflate (Hf(OTf)₄). Again, the reaction is performed neat at a temperature of 175° C. for 3 h.

Scheme 2: FDM acylation reaction as catalyzed by hafnium triflate.

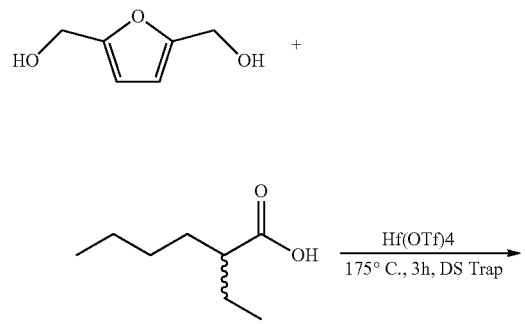

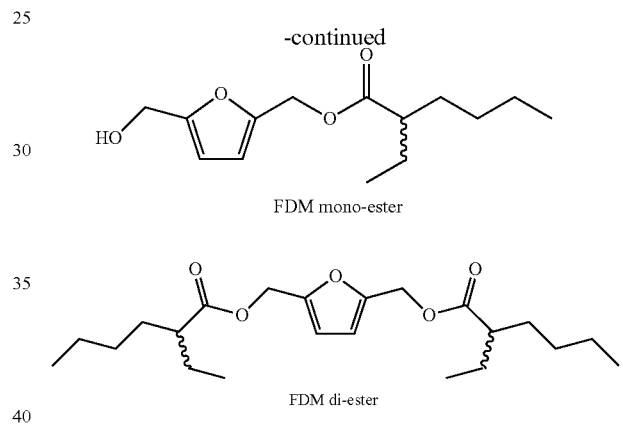

FDM mono-ester

FDM di-ester

Two examples of FDM esterification are summarized in Table 4. One example is run under a catalyst load at 0.1 mol. % and the other at 0.01 mol. % relative to the amount of FDM. In both examples, all of the FDM converted to either the mono or diester species. This efficient conversion is believed to reflect the high activity of the hafnium triflate catalyst. At a catalyst amount of 0.1 mol. % all of the FDM converts completely to the diester. At a catalyst amount of 0.01% about half of the FDM converts to the diester, while about 40% remains in the monoester form. A greater catalyst load appears to enhance full conversion to the diester product.

TABLE 4

FDM Esterification

| Ex. | Catalyst | Catalyst Loading (mol. %) | Time (h) | Temp (° C.) | Conversion (wt. % FDM) | FDM mono-2EH wt. % | FDM di-2EH wt. % | Product Accountability |
|---|---|---|---|---|---|---|---|---|
| 1 | Hf(OTf)₄ | 0.1 | 3 | 175 | 100 | 0 | 100 | 86 |
| 2 | Hf(OTf)₄ | 0.01 | 3 | 175 | 100 | 39 | 52 | 91 |

The reactions exhibit compositional accountability of 86% and 91% (39 mol. % monoester+52 mol. % diester) for the product mixture, respectively for the 0.1 mol. % and 0.01 mol. % catalyst loads. Again, these values are comparable to or better than the product accountability for conventional esterification processes using sulfuric acid catalyst.

Section II.—Examples

The following examples are provided as illustration of the different aspects of the present disclosure. Changes in parameters and conditions (e.g., changes of temperature, time and reagent concentrations, and particular starting species and catalysts) can affect and extend the full practice of the invention.

A. bHMTHF Acylation

Example 1

Figure 4:
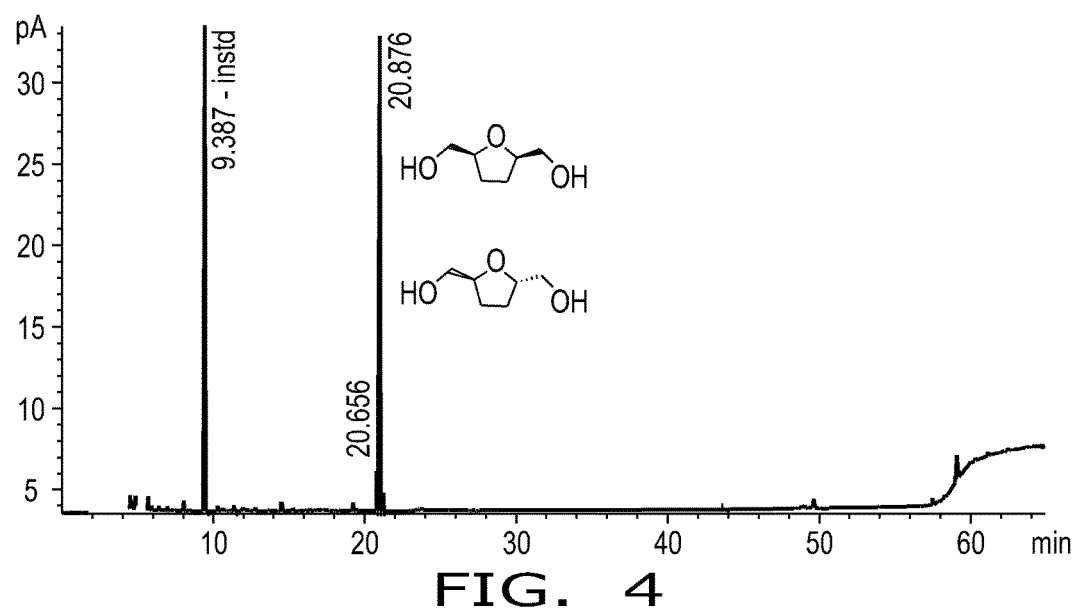
FIG. 4, is a standard gas chromatographic (GC) trace of bHMTHF stereoisomers.
Figure 5:
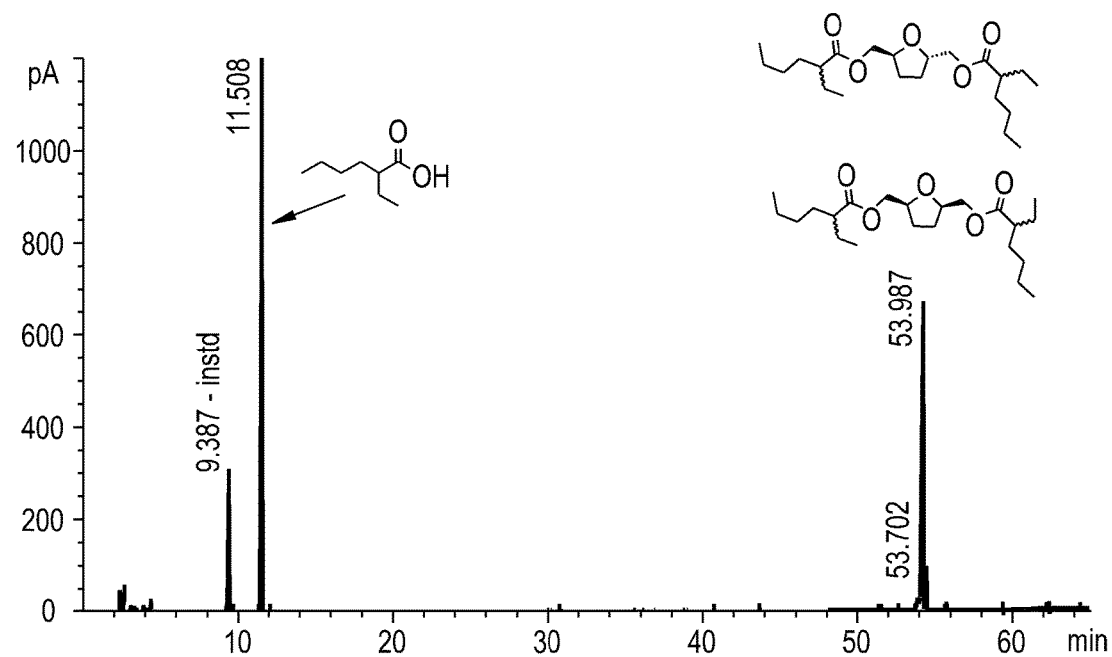
FIG. 5, is a gas chromatographic (GC) trace of bHMTHF esterification catalyzed by 0.1 mol % $Bi(OTf)_3$.

Acylation of bHMTHF with 2-ethylhexanoic acid, catalyzed by 0.1 mol % Bi(OTf)$_3$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 49.7 mg of bismuth triflate (0.1 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by gas chromatographic (GC) (silanation). In comparison to the GC trace of the bHMTHF precursor shown in FIG. 4, FIG. 5 displays the resulting trace divulged full conversion of bHMTHF to the corresponding diester.

Example 2

Figure 6:
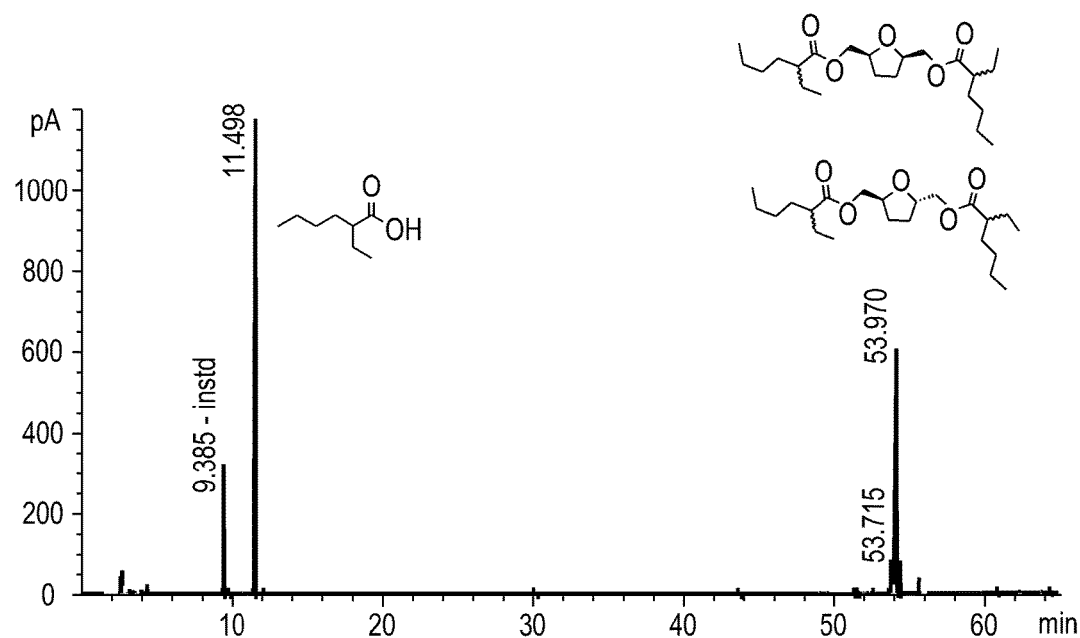
FIG. 6, is a gas chromatographic (GC) trace of bHMTHF acylation with 2-ethylhexanoic acid catalyzed by 0.1 mol % $In(OTf)_3$.

Acylation of bHMTHF with 2-ethylhexanoic acid catalyzed, by 0.1 mol % In(Otf)$_3$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 42.7 mg of indium triflate (0.1 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). FIG. 6 shows the resulting trace divulged full conversion of bHMTHF to the corresponding diester.

Example 3

Figure 7:
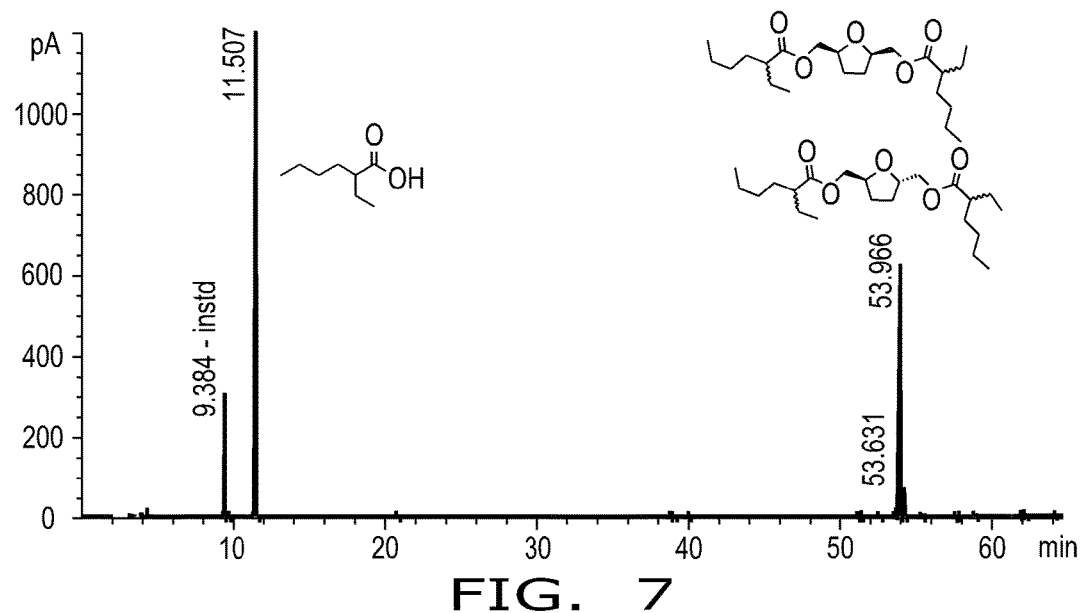
FIG. 7, is a gas chromatographic (GC) trace of bHMTHF acylation with 2-ethylhexanoic acid catalyzed by 0.1 mol % $Ga(OTf)_3$.
Figure 8:
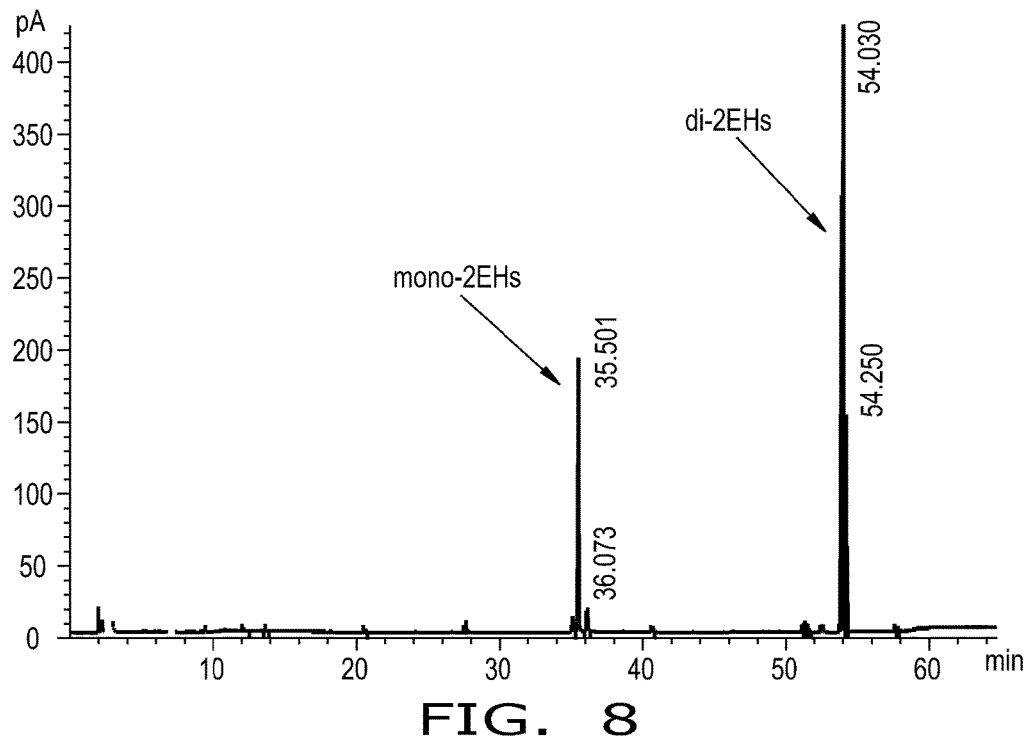
FIG. 8, is a gas chromatographic (GC) trace of bHMTHF acylation with 2-ethylhexanoic acid catalyzed by 0.1 mol % $Sn(OTf)_2$.

Acylation of bHMTHF with 2-ethylhexanoic acid, catalyzed by 0.1 mol % Ga(OTf)$_3$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 39.3 mg of gallium triflate (0.1 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). FIG. 7 presents the resulting trace divulged full conversion of bHMTHF to the corresponding diester.

Example 4

Acylation of bHMTHF with 2-ethylhexanoic acid, catalyzed by 0.1 mol % Sn(OTf)$_2$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 31.7 mg of tin triflate (0.1 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). FIG. 7 shows the resulting trace divulged full conversion of bHMTHF to the primarily the diester.

Example 5

Figure 9:
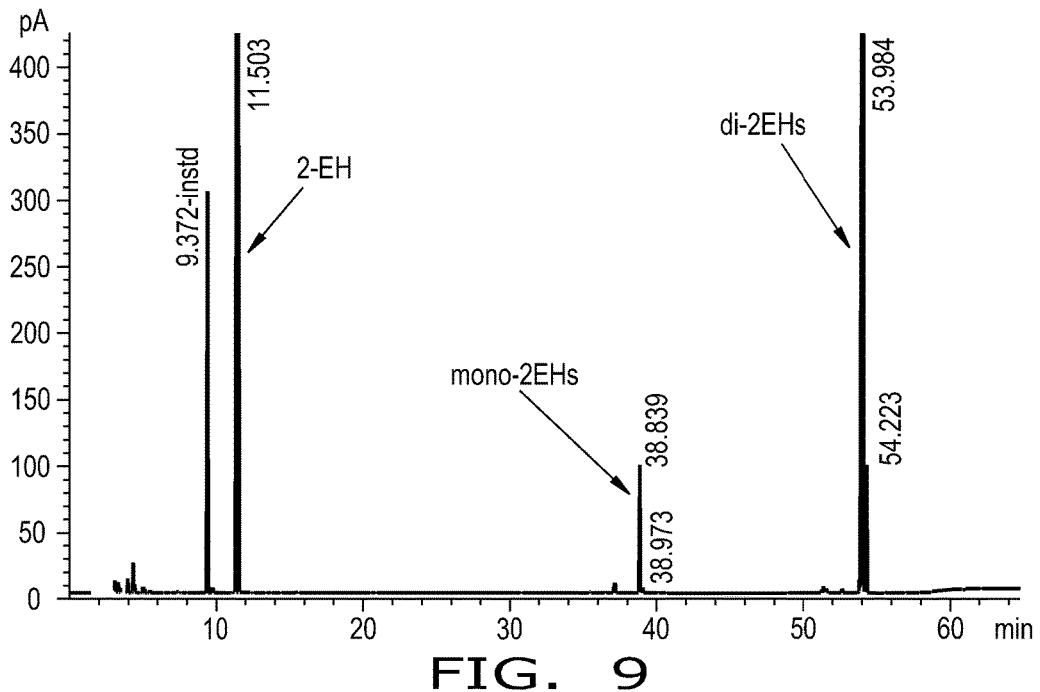
FIG. 9, is a comparative gas chromatographic (GC) trace of bHMTHF acylation with 2-ethylhexanoic acid catalyzed by 0.1 mol % sulfuric acid.

Acylation of bHMTHF with 2-ethylhexanoic acid, catalyzed by 0.1 mol % H$_2$SO$_4$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 7.45 mg of sulfuric acid (0.01 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). The resulting trace divulged partial conversion of bHMTHF to, primarily, the mono-2EH ester with an iota of di-2EH (FIG. 9, vide infra)

Comparative Example

Figure 10:
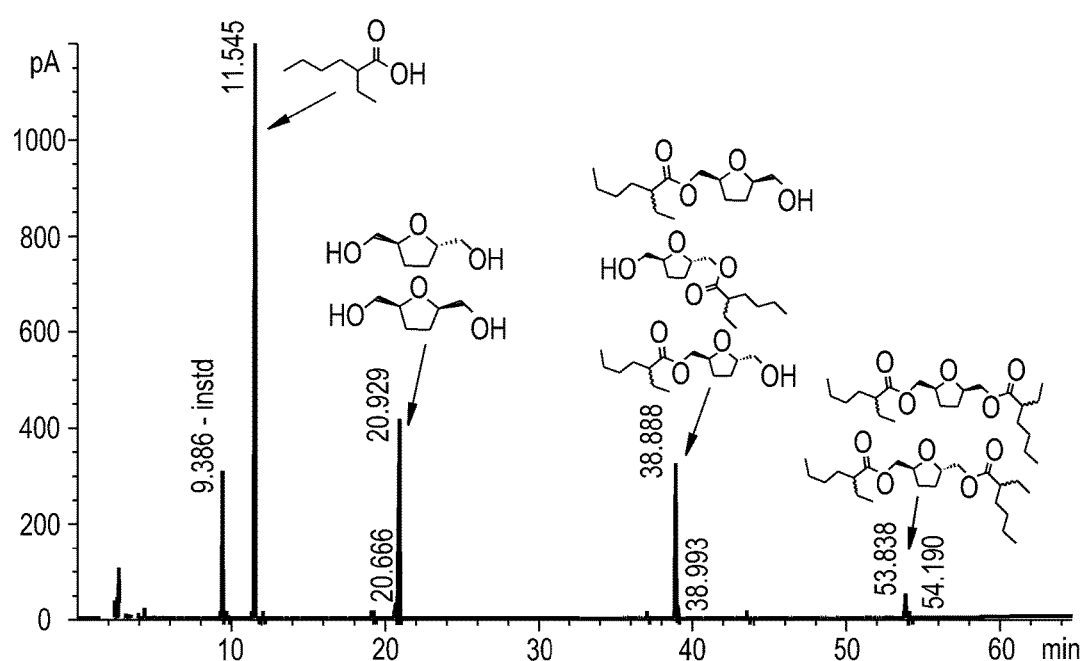
FIG. 10, is a comparative gas chromatographic (GC) trace of bHMTHF acylation with 2-ethylhexanoic acid catalyzed by 0.01 mol % sulfuric acid.

Acylation of bHMTHF with 2-ethylhexanoic acid, catalyzed by 0.01 mol % H$_2$SO$_4$. Experimental: A three neck 100 mL round bottomed flask containing a PTFE magnetic stir bar was charged with 10 g of bHMTHF (0.076 mmol), 40 g of 2-ethylhexanoic acid (0.277 mmol) and 0.745 mg of sulfuric acid (0.01 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). The resulting trace divulged partial conversion of bHMTHF to, primarily, the mono-2EH ester with an iota of di-2EH (FIG. 10).

B. FDM Acylation

Example 1. Acylation of FDM with 2-Ethylhexanoic Acid, Catalyzed by 0.1 Mol % Hf(OTf)₄

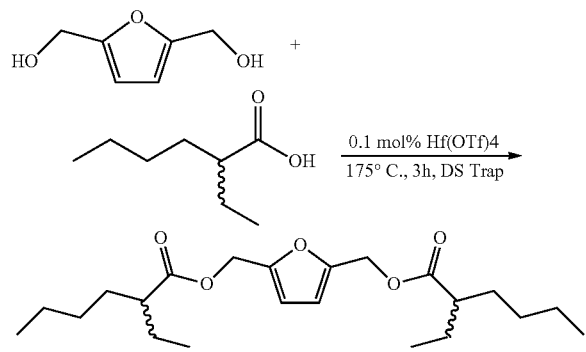

Experimental: A three neck 100 mL round bottomed flask containing a PTFE magnetic stir bar was charged with 10 g of FDM (0.078 mmol), 40 g of 2-ethylhexanoic acid (0.277 mmol) and 60.5 mg of hafnium triflate (0.1 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). The corresponding chromatogram disclosed that all the FDM had been converted (no signature peak at 21.23 min retention) to only the diester (signature retention time of 54.76 min).

Example 2. Acylation of FDM with 2-ethylhexanoic acid, catalyzed by 0.01 mol % Hf(OTf)₄

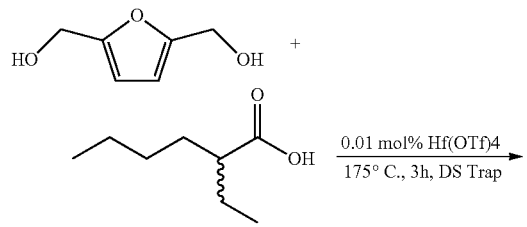

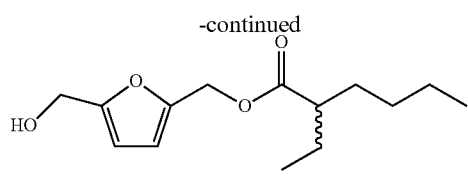

FDM mono-ester

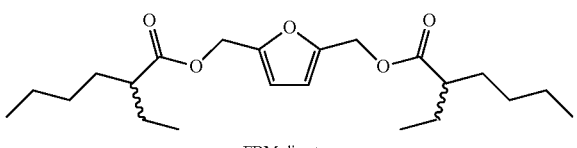

FDM di-ester

Experimental: A three neck 100 mL round bottomed flask containing a PTFE magnetic stir bar was charged with 10 g of FDM (0.078 mmol), 40 g of 2-ethylhexanoic acid (0.277 mmol) and 6.1 mg of hafnium triflate (0.01 mol %). The leftmost neck of the flask was then adhibited to jacketed Dean-Stark trap stoppered with a rubber septum that was pierced by three 14" needles, the center neck capped with a ground glass sleeved thermowell adapter, and the rightmost a ground glass adapter affixed to an argon line. The flask was then immersed in a high temperature silicon oil bath. With a vigorous argon sweep and concomitant stirring, the mixture was heated to 175° C. for 3 hours. After this time, the product matrix was cooled to room temperature and an aliquot analyzed by GC (silanation). The corresponding chromatogram revealed that all the FDM had been converted (no signature peak at 21.23 min retention) to primarily the mono-ester (52 wt. %, signature retention time 37.34 min) and diester (36 wt. %, signature retention time of 54.76 min).

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently know or to be developed, which may be used within the scope of the invention. Therefore, unless changes otherwise depart from the scope of the invention, the changes should be construed as being included herein.

I claim:

1. A method for acid-catalyzed acylation of a reduction product of 5-(hydroxylmethyl)-furfural (HMF) comprising: contacting the reduction product of HMF with an excess of an organic acid in the presence of a water-tolerant Lewis acid catalyst at a reaction temperature and for a time sufficient to produce a corresponding ester product mixture.

2. The method according to claim 1, wherein said reduction product of HMF is either furan-2,5-dimethanol (FDM) or bis-2,5-hydroxymethyl-tetrahydrofuran (bHMTHF).

3. The method according to claim 1, wherein said organic acid is selected from the group consisting of an alkanoic acid, alkenoic acid, alkyonoic acid, and aromatic acid, having a carbon chain length ranging from $C_2$-$C_{26}$.

4. The method according to claim 1, wherein said organic acid is selected from the group consisting of 2-ethylhexanoic acid, hexanoic acid, and octanoic acid.

5. The method according to claim 1, wherein said reaction temperature is from about 150° C. to about 250° C.

6. The method according to claim 5, wherein said reaction temperature is from about 170° C. to about 220° C.

7. The method according to claim 1, wherein said reaction time is between 0.5 and 12 hours.

8. The method according to claim 7, wherein said reaction time is between about 1-4 hours.

9. The method according to claim 1, wherein ≥55% of said reduction product of HMF is converted to said corresponding ester product.

10. The method according to claim 9, wherein about 80% to 100% of said reduction product of HMF is converted.

11. The method according to claim 1, wherein at least 10% of the esters in said ester product mixture are diesters.

12. The method according to claim 11, wherein said yield of diester is from about 15% to about 85%.

13. The method according to claim 1, wherein said organic acid is present in about 2-fold to about 10-fold molar excess relative to an amount of said reduction product of HMF.

14. The method according to claim 13, wherein said organic acid is present in about 3-fold to about 5-fold molar excess.

15. The method according to claim 1, wherein said Lewis acid is a water-tolerant metal triflate selected from the group consisting of lanthanum triflate, cerium triflate, praseodymium triflate, neodymium triflate, samarium triflate, europium triflate, gadolinium triflate, terbium triflate, dysprodium triflate, holmium triflate, erbium triflate, ytterbium triflate, lutetium triflate, gallium triflate, scandium triflate, bismuth triflate, hafnium triflate, mercury triflate, iron triflate, nickel triflate, copper triflate, zinc triflate, thallium, tin triflate, indium triflate, and a combination thereof.

16. The method according to claim 15, wherein said metal triflate is at least one of: gallium triflate, scandium triflate, bismuth triflate, hafnium triflate, indium triflate, aluminum triflate, or tin triflate.

17. The method according to claim 1, wherein said metal triflate is at a catalyst load of about 0.001 mol. % to about 1 mol. % relative to the amount of HMF reduction product.

18. The method according to claim 17, wherein said metal triflate is present at about 0.01 mol. % to about 0.1 mol. %.

19. The method according to claim 1, wherein said ester product mixture has a percentage accountability of at least 80%.

20. The method according to claim 1, wherein said ester product mixture has at least the same level of accountability as a product mixture from a reaction catalyzed with a strong Brønsted at the same catalyst load.

\* \* \* \* \*